US006836682B2

(12) United States Patent
Van Dam (10) Patent No.: US 6,836,682 B2
(45) Date of Patent: Dec. 28, 2004

(54) RATE RESPONSIVE PACING SYSTEM WITH QT SENSOR BASED ON INTRINSIC QT DATA

(75) Inventor: Peter Van Dam, Doesburg (NL)

(73) Assignee: Medtronic, Inc., Minneapolis, MN (US)

(*) Notice: Subject to any disclaimer, the term of this patent is extended or adjusted under 35 U.S.C. 154(b) by 433 days.

(21) Appl. No.: 09/987,776

(22) Filed: Nov. 16, 2001

(65) Prior Publication Data
US 2003/0100926 A1 May 29, 2003

(51) Int. Cl.⁷ .............................................. A61N 1/365
(52) U.S. Cl. ........................................ 607/25; 607/26
(58) Field of Search ............................. 607/25, 17, 26; 600/515, 516, 521

(56) References Cited

U.S. PATENT DOCUMENTS

| 4,228,803 | A | 10/1980 | Rickards |
| 4,305,396 | A | 12/1981 | Wittkampf et al. |
| 4,316,472 | A | 2/1982 | Mirowski et al. |
| 4,375,817 | A | 3/1983 | Engle et al. |
| 4,379,459 | A | 4/1983 | Stein |

(List continued on next page.)

FOREIGN PATENT DOCUMENTS

EP 0 148 486 7/1985 ........... A61N/1/368

OTHER PUBLICATIONS

US 4,384,588, 5/1983, Zipes (withdrawn)

"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp 167–170.

"Automatic Tachycardia Recognition" Arzbaecher et al. PACE, May–Jun. 1984 p. 541–547.

Primary Examiner—Kennedy Schaetzle
(74) Attorney, Agent, or Firm—Girma Wolde-Michael; Daniel G. Chapik (57) ABSTRACT

There is provided a system and method of rate responsive pacing, having an intrinsic QT rate sensor. The system has the capability of sensing the QT interval of intrinsic cardiac signals and constructing from such intrinsic QT data a QT reference curve. The QT reference curve is used for comparison with beat-to-beat QT interval data, in order to provide sensor information for controlling pacing rate. The system of this invention preferably utilizes DSP circuitry for determining the occurrence of a Twave event and the timing of the Twave, from which the QT interval is calculated. The system also provides for compensation of any QT interval which is calculated following ventricular pacing, so that the QT sensor is operative at all times and throughout the entire rate range experienced by the patient. The system thereby provides an enhanced QT rate responsive pacing arrangement, and avoids the need of overdrive pacing in order to obtain QT reference data.

34 Claims, 8 Drawing Sheets

U.S. PATENT DOCUMENTS

| | | |
|---|---|---|
| 4,476,868 A | 10/1984 | Thompson et al. |
| 4,556,063 A | 12/1985 | Thompson et al. |
| 4,577,638 A | 3/1986 | Graham |
| 4,587,970 A | 5/1986 | Holley et al. |
| 4,644,954 A | 2/1987 | Wittkampf et al. |
| 4,726,380 A | 2/1988 | Vollmann et al. |
| 4,727,877 A | 3/1988 | Kallok |
| 4,800,883 A | 1/1989 | Winstrom |
| 4,821,723 A | 4/1989 | Baker et al. |
| 4,880,005 A | 11/1989 | Pless et al. |
| 4,949,719 A | 8/1990 | Pless et al. |
| 4,953,551 A | 9/1990 | Mehra |
| 4,972,834 A | 11/1990 | Begemann et al. |
| 5,099,838 A | 3/1992 | Bardy |
| 5,117,824 A | 6/1992 | Keimel et al. |
| 5,131,388 A | 7/1992 | Pless et al. |
| 5,144,949 A | 9/1992 | Olson |
| 5,158,078 A | 10/1992 | Bennett et al. |
| 5,163,427 A | 11/1992 | Keimel |
| 5,188,105 A | 2/1993 | Keimel |
| 5,199,428 A | 4/1993 | Obel et al. |
| 5,207,218 A | 5/1993 | Carpenter et al. |
| 5,269,298 A | 12/1993 | Adams et al. |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennett et al. |
| 5,354,316 A | 10/1994 | Keimel |
| 5,470,344 A | 11/1995 | Begemann |
| 5,545,186 A | 8/1996 | Olson |
| 5,560,368 A * | 10/1996 | Berger ............... 600/517 |
| 5,690,686 A | 11/1997 | Min et al. |
| 5,782,887 A | 7/1998 | Van Krieken et al. |
| 5,800,465 A | 9/1998 | Maeda et al. |
| 5,978,711 A | 11/1999 | Van Hove |

\* cited by examiner

RATE RESPONSIVE PACING SYSTEM WITH QT SENSOR BASED ON INTRINSIC QT DATA

FIELD OF THE INVENTION

This invention relates to implantable rate responsive cardiac pacemaker systems and methods for rate control of cardiac pacing and, more particularly, rate responsive pacemaker systems that have the capability of adjusting the pacing rate as a function of QT interval.

BACKGROUND OF THE INVENTION

Implantable rate responsive pacemakers and other implantable medical devices that include rate responsive pacing have been in existence for some years. In a normal patient who undertakes exercise or becomes involved in a stressful situation that calls for an increased heart rate, the patient's normal feedback mechanisms provide for the desired increased rate. However, for a variety of reasons the patient's normal feedback mechanisms may be impaired. For a single chamber ventricular pacing system, or if the intrinsic atrial rate is unreliable, the pacemaker must carry out the task of determining the physiologically desired rate. Rate responsive pacing systems have the aim of providing a substantially physiologic pacing rate by sensing one or more patient parameters and correlating desired rate with such parameters. Rate responsive pacemakers are available as single chamber or dual chamber pacemakers.

A variety of sensors for determining a desired pacing rate are known in the pacing art. The assignee of this invention has utilized the QT interval ("QT") as a parameter that is responsive to patient demand. The QT interval is the time between contraction of the heart and the relaxation of the heart. This is manifested by electrical signals which are measured by the implantable device when the depolarization/repolarization waves pass the electrode system implanted within the patient's heart. The QT interval can be thought of as having a rate dependent component and a stress dependent component. The rate dependent component causes the QT interval to shorten at higher rates as the heart pumps more often and therefore reduces the time it stays contracted. Conversely, the QT interval lengthens at lower rates. The stress level, either physical or mental, also causes a QT interval shortening at times of higher stress. Thus, when QT interval is measured at any given rate, its value can be based both on the rate dependent component and the stress component. In healthy hearts the QT interval will always correspond to the desired heart rate, and thus can be used as a sensor for the metabolic need of the patient.

The QT sensor, to be effective, must have knowledge of the expected QT interval corresponding to any given rate. This is generally accomplished by maintaining within the pacemaker a QT reference curve, also referred to as a QT (RR) curve. If the QT interval at a given rate is shorter than the corresponding reference curve value at that rate, this indicates that the pacemaker should start pacing at a higher rate. In prior art QT sensor systems, the QT interval has been measured only after a ventricular pace, for the reason that it is difficult to sense the T wave following an intrinsic QRS signal. In pacing, the depolarization wave, or QRS complex, starts at the lead electrode or electrodes where the stimulus is delivered, such that the "Q" time is actually the stimulus time. Further, the Twave that results from a stimulus delivered through an electrode positioned adjacent the lead tip is reliably detected. However, in the case of an intrinsic QRST complex, the Twave comes from above the lead position, and can travel different routes, is less well defined and more difficult to sense. For this reason, QT rate responsive pacemakers have relied upon obtaining QT measurements in response to delivered pacing pulses. These are actually Stim-T values, measured from the time of delivery of the stimulus pulse. In such a system, when the patient's heart is naturally providing intrinsic QRST complexes, it is not possible to update or adjust the QT (RR) reference curve. In such circumstances, the QT rate responsive pacemaker historically has periodically initiated a pacing overdrive routine, to capture the heart with higher rate pacing so as to obtain QT (RR) reference data. However, the overdrive feature is not desirable, as it paces the patient at a rate that isn't called for. Further, it is not able to provide reference data throughout the normal range of the patient's intrinsic cardiac activity.

There are several problems with obtaining QT interval from intrinsic beats. As noted, it is more difficult to detect the intrinsic T wave, which is not as well defined and has a smaller amplitude than does the T wave that follows an evoked QRS. The QT interval in the sensed case is shorter than that in the paced case. Further, the intrinsic ventricular contraction might originate from an ectopic focus, which in turn can cause a deviation from the QT interval anticipated when the ventricular contraction originates from the AV node. These problems must be overcome in any arrangement for sensing intrinsic QT intervals.

Examples of pacing systems incorporating a QT rate responsive pacing, as well as techniques for adjusting the QT reference curve, are listed in Table 1 below. Also listed are patents showing the use of DSP technology for determination and classification of a sensed cardiac event.

TABLE 1

| Patent No. | Inventor(s) | Issue Date |
| --- | --- | --- |
| 4,228,803 | Rickards | October, 1980 |
| 4,972,834 | Begemann et al | Nov. 27, 1990 |
| 5,065,759 | Begemann et al | Nov. 19, 1991 |
| 5,470,344 | Begemann | Nov. 28, 1995 |
| 5,978,711 | Van Hove | Nov. 2, 1999 |
| 6,029,087 | Wohlgemuth | Feb. 22, 2000 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the teachings of the present invention.

SUMMARY OF THE INVENTION

It is an object of this invention to provide an improved rate responsive pacing system that utilizes QT as the sensor parameter for determining desired pacing rate. It is a further object this invention to provide such a system and method of pacing which obtains values of both intrinsic and evoked QT, and constructs a QT (RR) reference curve across the full range of the patient activity. A further object is to provide a pacing system and method of rate control that utilizes a QT sensor and does not need to resort to overdrive pacing in order to get QT information.

In accordance with the above objects, there is provided a rate responsive pacemaker and system of controlling pacing rate that utilizes QT interval data obtained from intrinsic heartbeats. The system and method of this invention accomplish the above object by utilizing DSP or equivalent circuit technology in combination with software to recognize intrinsic Twaves and to determine QT intervals continuously whether the patient is being paced or whether the patient has an intrinsic heartbeat. A preferred algorithm for reliably detecting the intrinsic T wave provides for integration of the sensed signal for a predetermined time window following the QRS complex, and determines the time of a detected T wave by timing either the maximum of the T wave slope or the maximum amplitude of the T wave. QT data obtained during pacing is compensated to take into the account the difference between the stimulus-T wave time following the delivery of the pacing stimulus, and the intrinsic QT time interval.

It is a further object of this invention to recognize any ventricular contraction that is an ectopic focus, and to discriminate and not use such sensed ectopic beats for adjustment of the QT reference curve. This is accomplished by recognition of the different profile, or shape of the QRS complex of an ectopic beat, as compared to the normal depolarization wave. DSP technology is suitably used for event classification and identification, in order to discriminate ectopic beats.

The system and method of this invention can be utilized as well in a pacemaker or implanted cardiac devise that utilizes more than one sensor for determining a desired pacing rate. For example, U.S. Pat. No. 5,065,759 illustrates a dual sensor pacemaker which utilizes both QT and activity sensing. As stated in that patent, which is listed above in Table 1, the QT sensor supplements an activity sensor, and can provide important information when the patient is undergoing stress without being characterized by a level of activity that would indicate the desired pacing rate.

DESCRIPTION OF THE PREFERRED EMBODIMENTS

Figure 1:
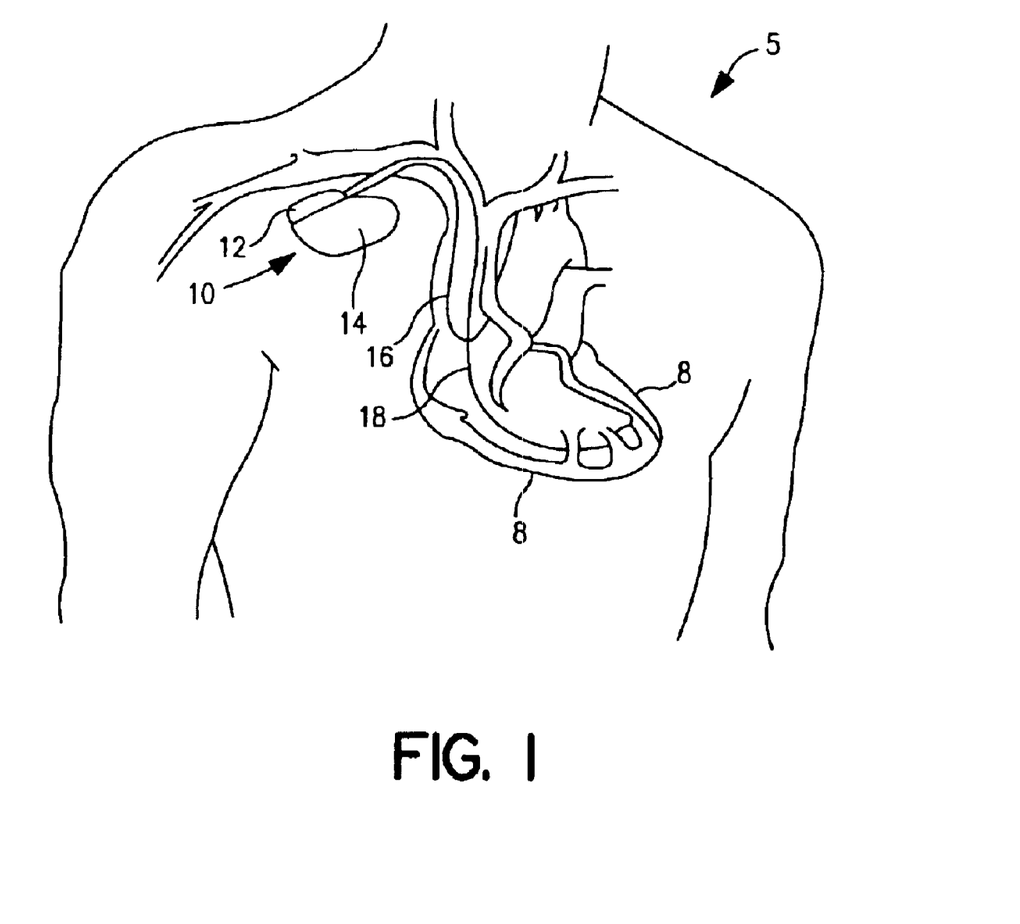
FIG. 1 is a simplified schematic view of one embodiment of an implantable medical device that can be employed in the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
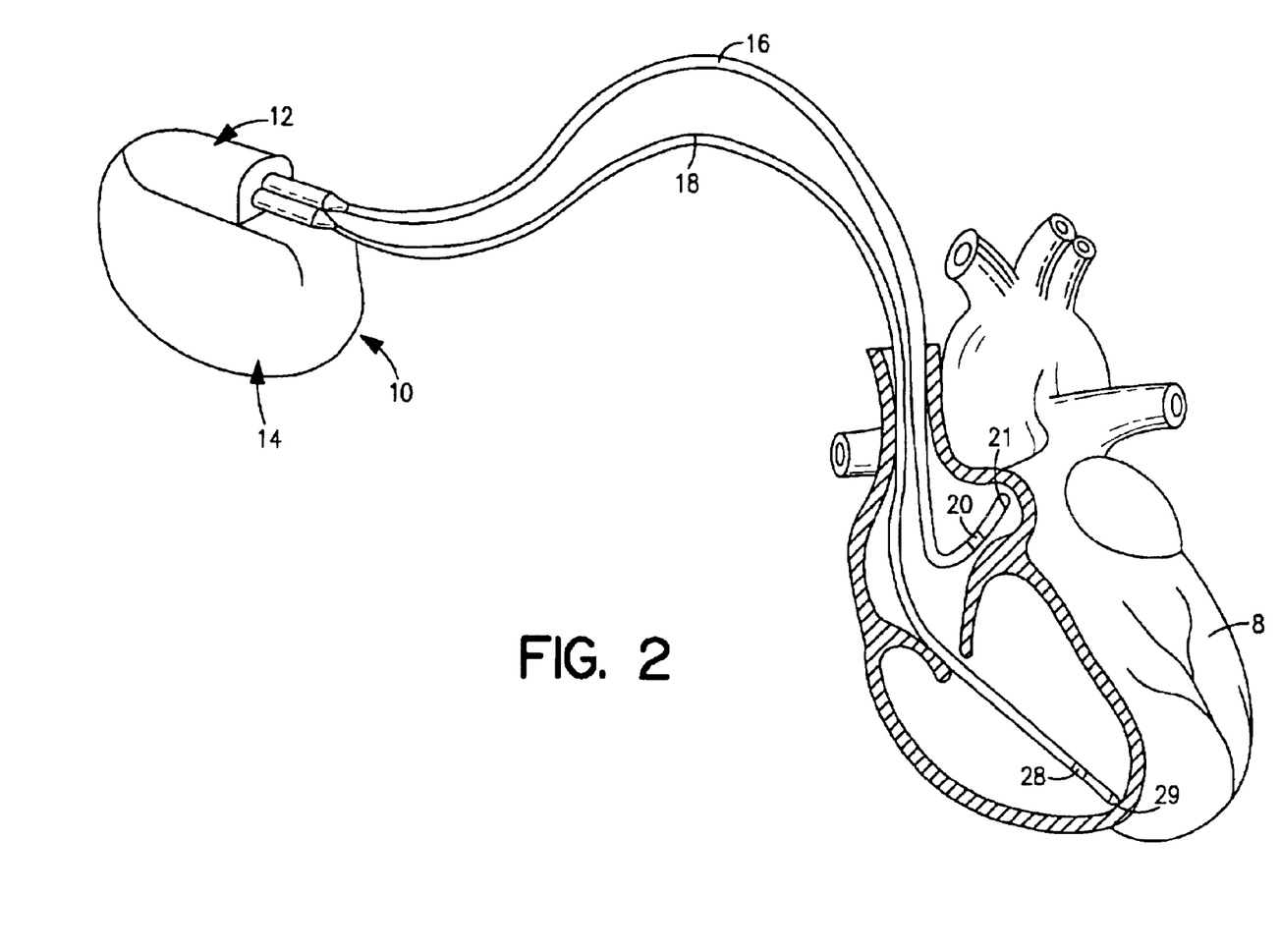
FIG. 2 is a graphic representation of an implantable medical device interconnected with a human or mammalian heart, illustrating the device connector portion and the leads between the device and the heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
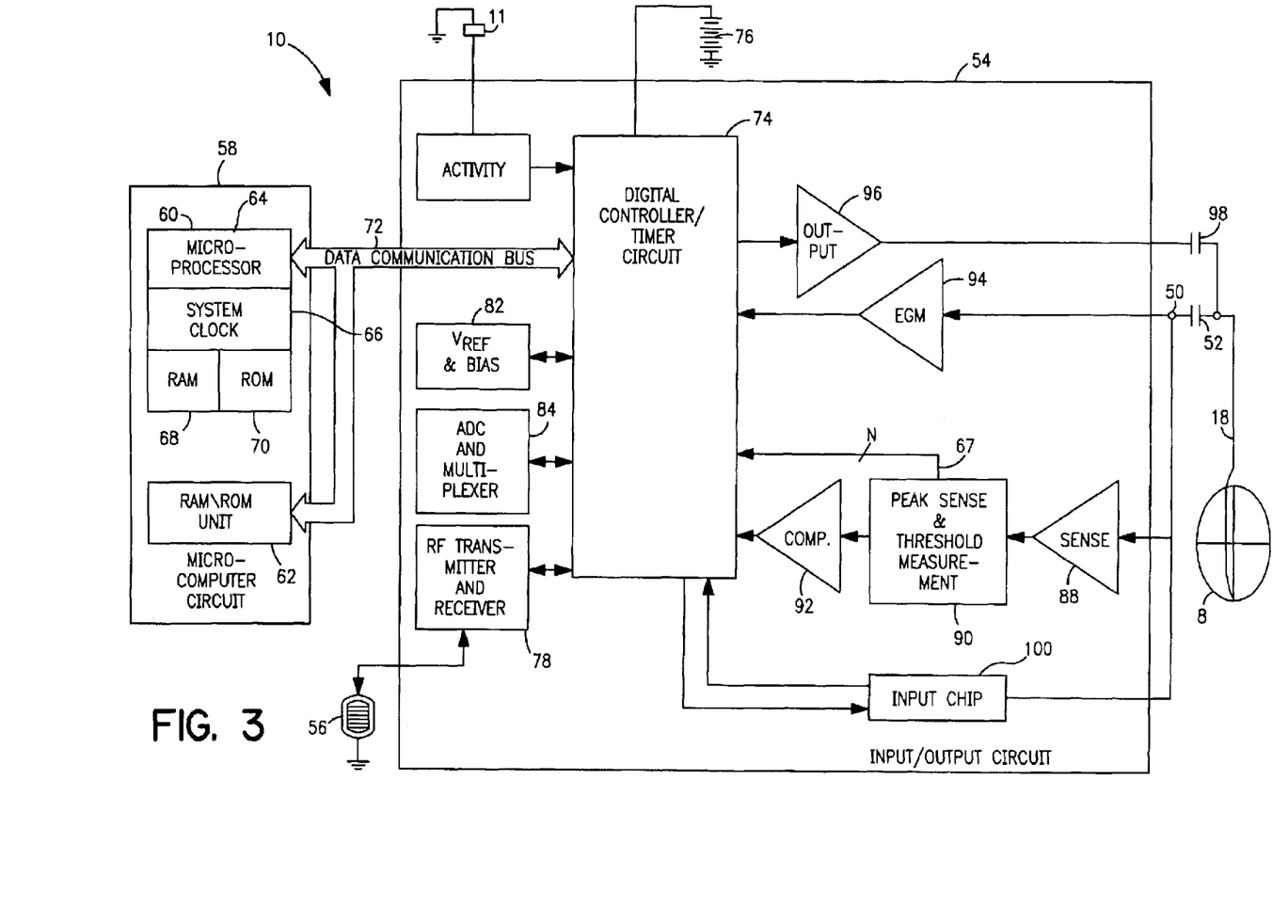
FIG. 3 is a functional schematic diagram showing the primary constituent components of an implantable medical device in accordance with an embodiment of this invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al's '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, or an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. In the preferred embodiment, signals from the patient's heart are coupled to an input channel chip shown at 100, which chip provides outputs to the controller 74. The preferred embodiment of this chip incorporates DSP circuitry for identifying ectopic beats, as discussed in connection with FIG. 6 below, and as is further disclosed in U.S. Pat. No. 6,029,087, incorporated herein by reference. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
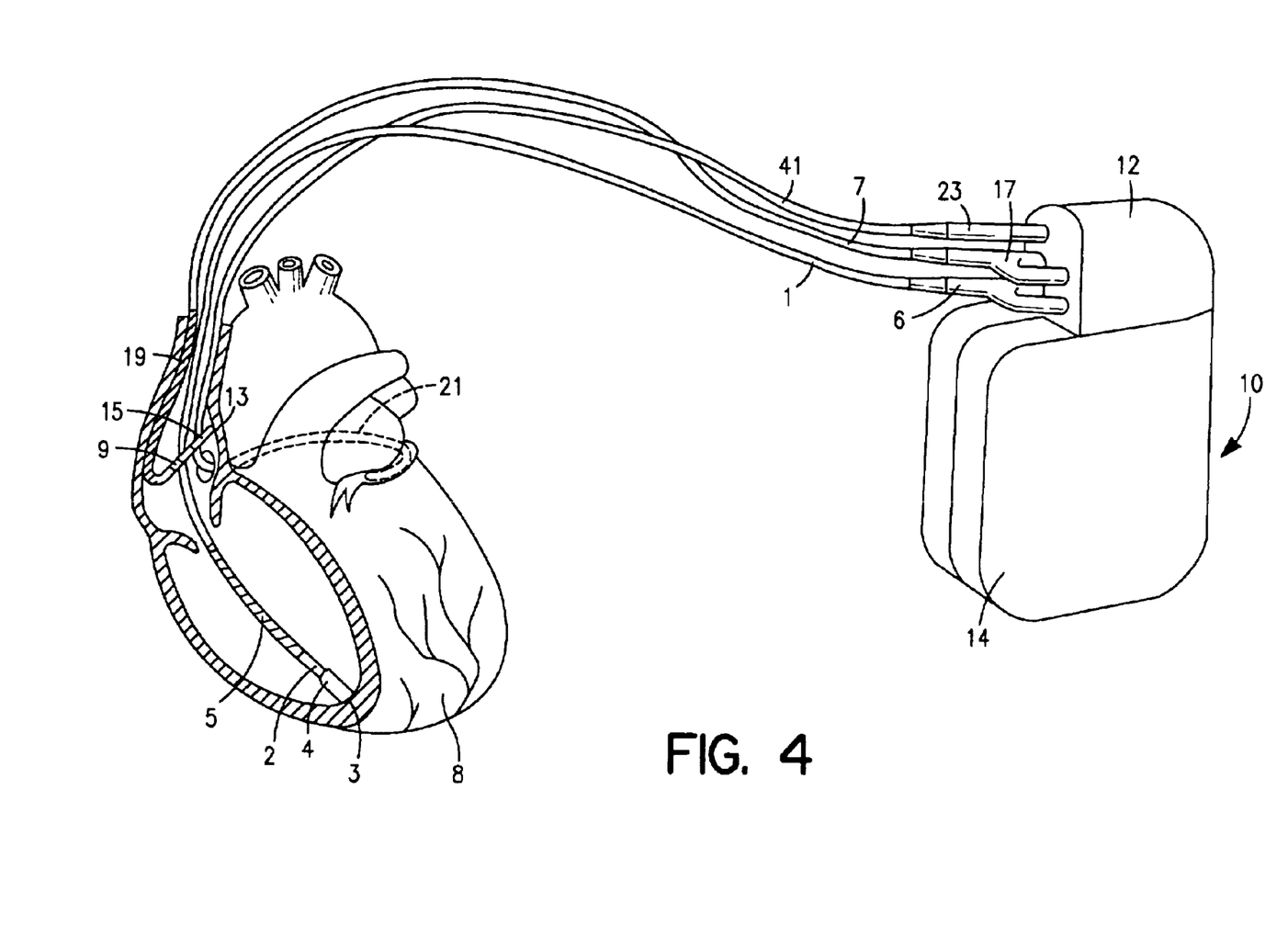
FIG. 4 is a graphic representation of an embodiment of this invention showing an implantable PCD device interconnected with a heart, the system of this embodiment providing pacing, cardio version and defibrillation.
Figure 5:
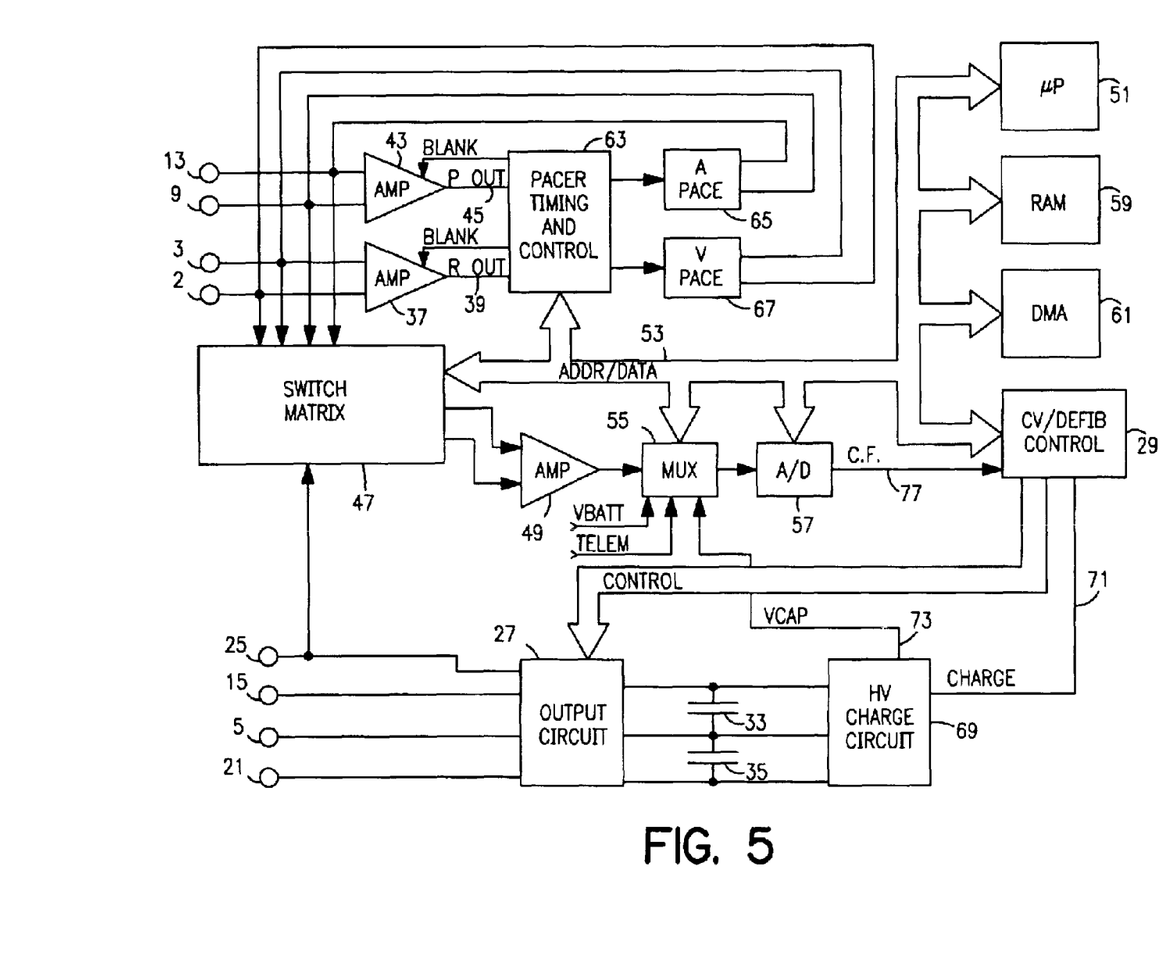
FIG. 5 is a functional schematic diagram of an implantable PCD embodiment of this invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths.

Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P–R intervals and R–P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat.

No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
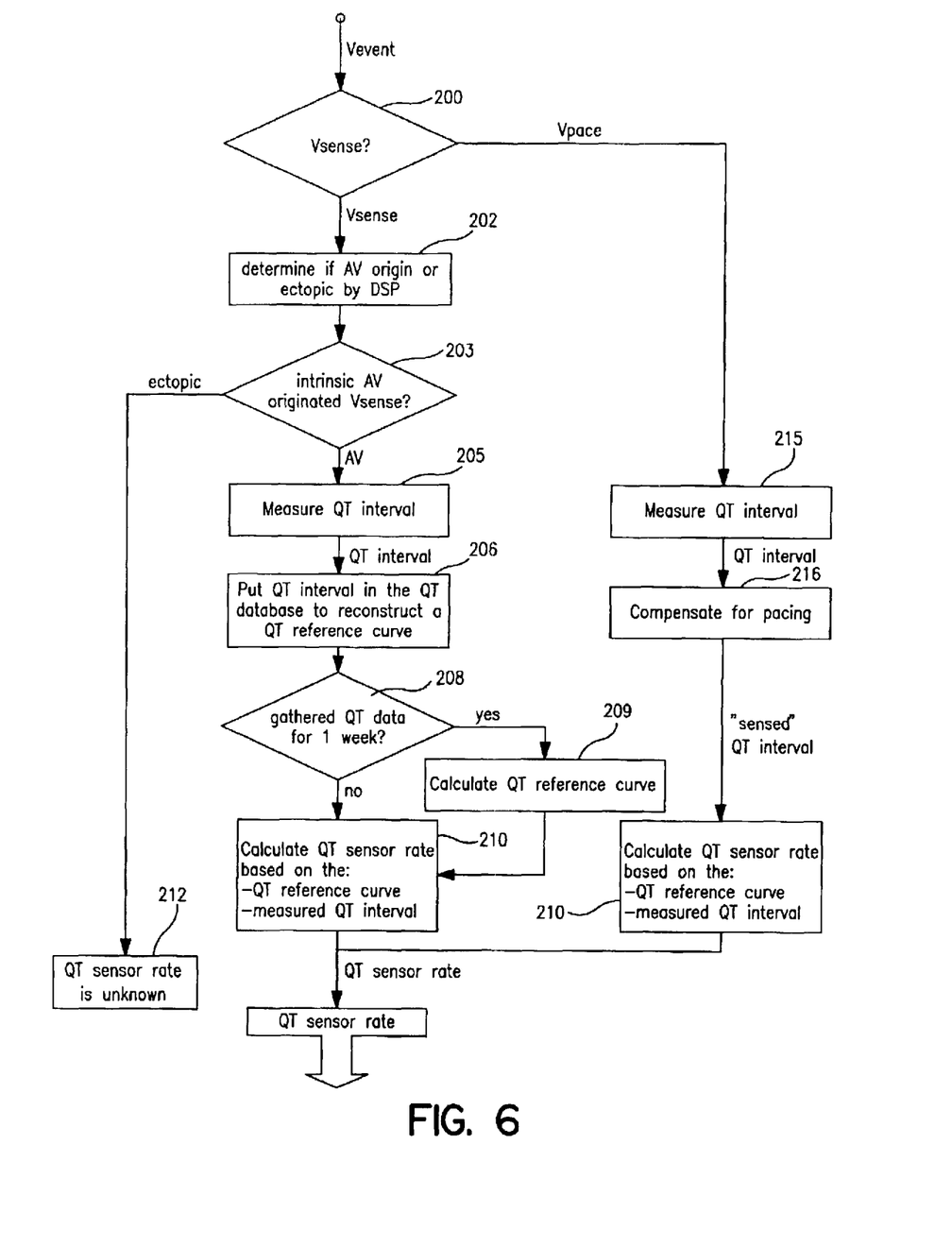
FIG. 6 is a flow diagram of a routine cardiac cycle.

FIG. 6 illustrates the overall routine for determining the desired QT sensor rate on a cycle-by-cycle basis. The routine is run following each Vevent, sense or pace, starting at 200. A Vsense represents a detected R wave, and is determined in a known manner such as is disclosed in referenced U.S. Pat. No. 6,029,087. Whether a sense or a pace, the R—R interval of the cycle is timed out and stored. At 200 it is also determined whether the event has indeed been a sense. If a ventricular sense has been detected, the routine goes to block 202 and assigns to the DSP circuitry 100 the task of determining if the sense was AV in origin or ectopic. At 203, the routine branches to 212 if it has been determined that it was an ectopic sense. In this case, as discussed above, the QT interval cannot be accurately determined, and no QT data is stored before the routine exits.

If, at 203, it has been confirmed that the sense was intrinsic AV in origin, then at 205 the QT interval is measured. This is done in accord with the steps set forth in more detail in connection with FIG. 8. After QT interval has been determined, at 206 the QT interval data is placed into a database together with the rate for construction of a QT reference curve. At 208, it is determined whether QT data has been gathered for a predetermined period of time, indicated as one week. This is a programmable variable, and can be set by the physician as either a period of elapsed time or a predetermined number of patient cardiac cycles. If sufficient data has not been gathered, the routine goes to 210 and calculates QT sensor rate in the conventional manner, i.e., by comparing the measured QT interval to the QT reference curve. Such a calculation is illustrated in the prior art, e.g., U.S. Pat. Nos. 4,972,834 and 5,065,759. Following this, the QT sensor rate is utilized for control of pacing when and as the pacing is required.

If at block 208 sufficient data has been obtained and stored, than the routine branches to 209 and calculates a new QT reference curve. Techniques for adjusting QT reference curve are shown in the patent literature. See, for example, U.S. Pat. No. 4,972,834.

If the Vevent has been a Vpace, at 200 the routine branches to 215 and measures the QT interval (Stim-T) in the standard way. At 216, the QT interval is compensated for pacing. As discussed above, the QT interval in the event of pacing is the stimulus-T interval, and is longer than the intrinsic QT interval. For most patients, the difference will be substantially a constant throughout the pacing range, such that the compensation at block 216 may be performed simply by subtracting a predetermined number of milliseconds from the measured QT interval. The compensation adjustment is a programmable variable. The compensated QT data may be stored as part of this step, as part of the QT database. Following compensation, the compensated QT interval is used at block 210 to calculate the QT sensor rate.

It is to be noted that, while not shown, the compensated QT interval can also be stored and used to calculate the QT reference curve, in the same manner as done at blocks 208 and 209.

In the operation of the routine of FIG. 6, there is no rate limit on the collection of QT data. Thus, control of pacing rate is limited to a high rate limit, as is conventional in any rate responsive pacing system. However, it is desirable to obtain and store QT data at higher rates, and this routine enables measuring of the QT interval at rates above the sensor high rate limit. The gathered QT data is stored for diagnostic purposes, and can be compressed into histogram form or another form for storage until downloaded to an external programmer for analysis.

Figure 7:
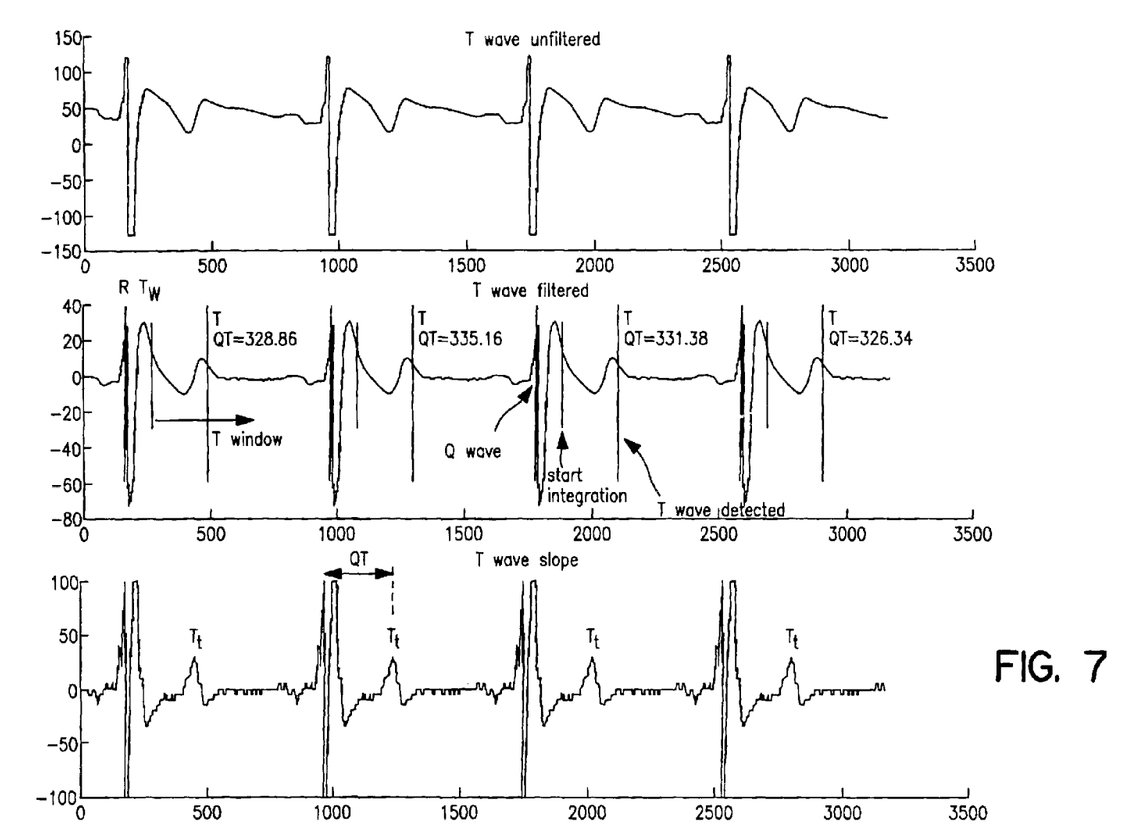
FIG. 7 shows three curves illustrating intrinsic Twaves and the manner of determining the intrinsic QT interval.
Figure 8:
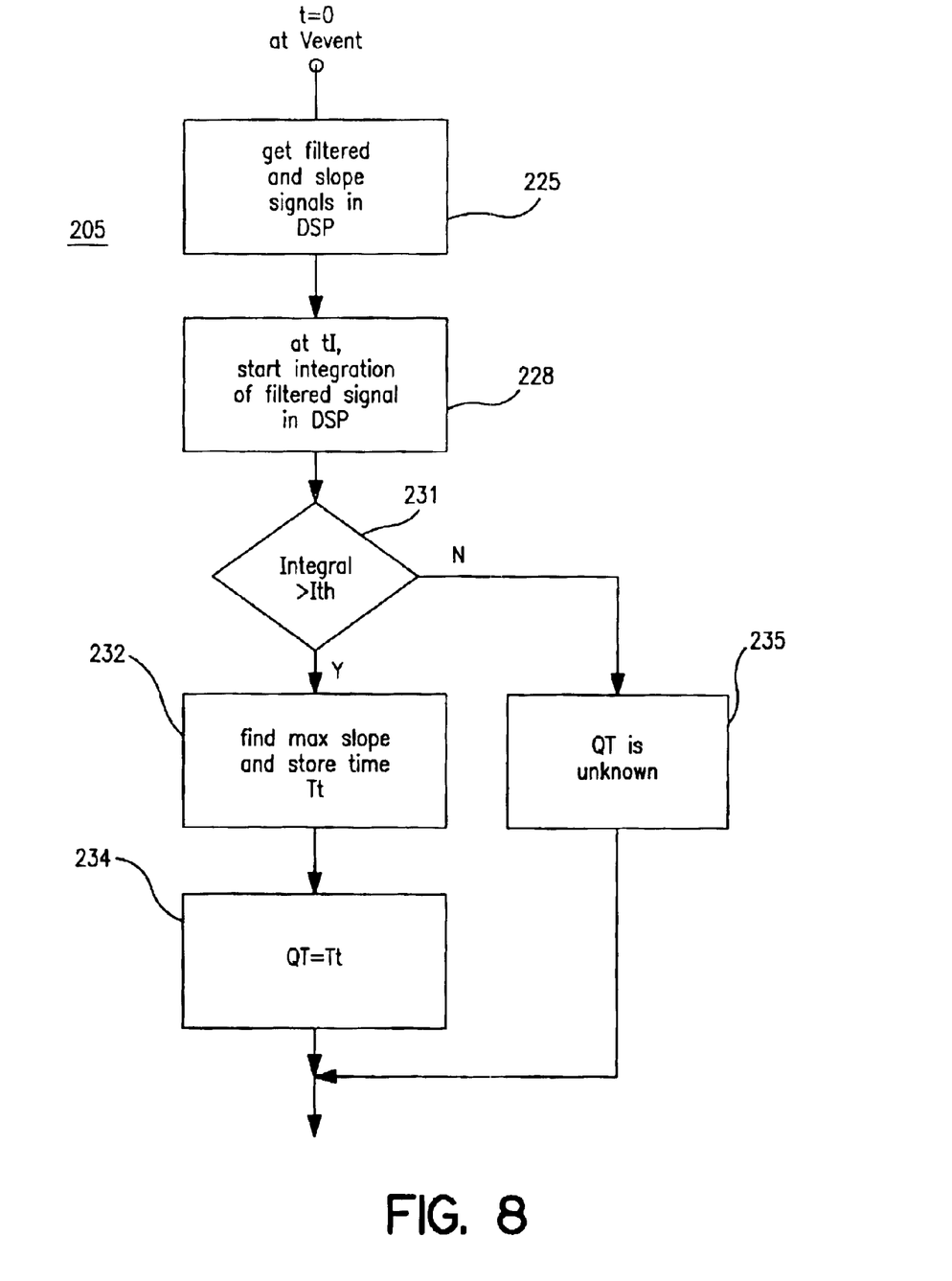
FIG. 8 is a flow diagram illustrating the steps taken in determining the occurrence of an intrinsic T wave event and for determining intrinsic QT interval.

FIG. 7 shows a series of curves that illustrate the preferred technique for determining QT interval for intrinsic cardiac signals. The top curve illustrates an unfiltered signal, such as is provided following amplification. The second curve shows a filtered signal, such as can be provided by the DSP circuitry illustrated in U.S. Pat. No. 6,029,087, incorporated herein by reference in its entirety. The timing of the R portion of the QRS wave is indicated by R. The Twave window is identified as T window and can be programmed to start at a predetermined delay following the peak R signal. The DSP circuitry integrates the total area of the curve following the start of the window, and identifies a T wave when the total integration becomes equal to a predetermined threshold. In the illustration of the middle curve, the T wave is identified as a T wave event by the vertical line marked T. Note that this signals detection of a T wave, but does not provide the timing of the T wave. The bottom curve of FIG. 8 illustrates the Twave slope, which also is available from the DSP circuitry in accord with the above referenced patent. The time of maximum slope during the Twave window is used as the time of occurrence of the T wave, indicated as $T_t$. The QT interval is shown as the time between the R wave and $T_t$.

FIG. 8 shows a flow diagram for measuring QT interval, which is step 205 in FIG. 6. At the time of the Vevent, whether a pace or a sense, a timer is initiated. Thus, at the start of the routine of FIG. 8, t=0. The clock continues to run during the course of executing this routine. At 225, the microprocessor sends control signals to the DSP circuitry, to generate the filtered Twave as seen in the middle curve of FIG. 7, as well as the Twave slope curve as seen in the bottom curve of FIG. 7. When time progresses to $T_w$, as shown in the middle curve of FIG. 7, integration of the filtered Twave is initiated, as illustrated at 228. The routine then proceeds to watch the value of the integral, and compares it to an integral threshold indicated at 231 as Ith. If the integral of the signal becomes greater than Ith, this indicates detection of a T wave. Then at 232 the routine finds the maximum slope, and gets the time $T_t$ of the occurrence of the maximum slope. This time is in fact QT, and at block 234 QT is set equal to $T_t$ and stored. However, if the integral never reaches Ith at 231, the routine exits to 235 and sets QT as unknown.

In the preferred embodiment of FIG. 8, the integral of the T wave is used as a measure of the T wave in order to detect the occurrence of a T wave. It is to be noted that other techniques may be used, within the scope of the invention, to detect the presence of a T wave. For example, morphology analysis may be utilized to obtain a "measure" of the T wave, as that term is used in the claims. Further, while the time of the maximum T wave slope signal is used in the preferred embodiment for identification of the T wave time, other measures of the T wave may be used.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to the use of DSP circuitry. The references to DSP do not exclude structures or operations that include some conventional analog circuitry. The present invention is also not limited to any particular combination of hardware and software per se, but may find further application with any form of software supplementing hardware. For example, other software embodiments that achieve the ability to efficiently store and manipulate the data, and analyze the T wave portion of the ventricular signal, are within the scope of the invention. The present invention further includes within its scope methods of making and using the QT sensor-driven pacing system described hereinabove.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A rate responsive pacing system having a pacemaker device and a lead system interconnecting said device and a patient's heart, said device having a pulse generator for generating pacing pulses, sensing means for sensing cardiac signals connected from said pulse generator to deliver pacing pulses at said sensor rate, said sensor means comprising:
   algorithm means for calculating a measure of the T wave portion of a received intrinsic cardiac signal;
   comparing means for comparing said measure with a predetermined criterion to detect the occurrence of the T wave portion of said signal;
   data means for determining and storing intrinsic QT interval data and heart rate data for each received intrinsic signal for which a T wave has been detected; and
   reference means for setting a QT reference curve as a function of said stored intrinsic QT interval and rate data, wherein said sensor means comprises high rate limit means for setting a maximum sensor rate, and wherein said algorithm means, said comparing means and said state means are operative at rates above said maximum sensor rate.

2. The system as described in claim 1, wherein said algorithm means comprises integration means for integrating said T wave portion, and said comparing means comprises programmable storage means for storing a threshold integral value that represents a valid T wave sense.

3. The system as described in claim 2, comprising Vpace means for determining when a ventricular pace has been delivered, second QT data means for determining evoked QT interval data and heart rate data, and compensating means for compensating said evoked QT interval data to account for the difference between intrinsic and invoked QT intervals.

4. The system as described in claim 3, wherein said second QT data means comprises slope means for detecting the occurrence of maximum T wave slope and for determining the time of said slope as the time of T wave occurrence.

5. A rate responsive pacing system having a pacemaker device and a lead system interconnecting said device and a patient's heart, said device having a pulse generator for generating pacing pulses, sensing means for sensing cardiac signals connected from said pulse generator to deliver pacing pluses at said sensor rate, said sensor means comprising:
   algorithm means for calculating a measure of the T wave portion of a received intrinsic cardiac signal;
   comparing means for comparing said measure with a predetermined criterion to detect the occurrence of the T wave portion of said signal;
   data means for determining and storing intrinsic QT interval data and heart rate data for each received intrinsic signal for which a T wave has been detected;
   reference means for setting a QT reference curve as a function of said stored intrinsic QT interval and rate data; and
   second algorithm means for determining and storing values of evoked QT interval for evoked cardiac signals, and wherein said rate control means comprises calculating means for calculating sensor rate following a ventricular event as a function of said QT reference curve and the evoked QT interval.

6. The system as described in claim 5, wherein said second algorithm means comprises compensation means for compensating each determined value of evoked QT interval to correspond to an intrinsic QT interval at the same rate.

7. The system as described in claim 6, wherein said compensation means comprises ms means for adjusting each determined value of evoked QT interval by a predetermined ms value, thereby compensating for the difference in measurements of intrinsic and evoked QT intervals.

8. The system as described in claim 5, wherein said data means has storage for storing data for a predetermined time, and whereas said reference means comprises means for calculating said QT reference curve when said data has been stored for said predetermined time.

9. The system as described in claim 8, wherein said reference means comprises time means for calculating said reference curve when data has been stored for a time period in the range of one day to one month.

10. A rate responsive pacing system having a pacemaker device and a lead system interconnecting said device and a patient's heart, said device having a pulse generator for generating pacing pulses, sensing means for sensing cardiac signals connected from said pulse generator to deliver pacing pulses at said sensor rate, said sensor means comprising:
    algorithm means for calculating a measure of the T wave portion of a received intrinsic cardiac signal;
    comparing means for comparing said measure with a predetermined criterion to detect the occurrence of the T wave portion of said signal;
    data means for determining and storing intrinsic QT interval data and heart rate data for each received intrinsic signal for which a T wave has been detected;
    reference means for setting a QT reference curve as a function of said stored intrinsic QT interval and rate data; and
    ectopic means for determining when a sensed cardiac signal represents an ectopic beat, and for setting said sensor rate as unknown for any such ectopic beat.

11. The system as described in claim 10, wherein said ectopic means comprises DSP circuitry for analyzing the shape of a sensed cardiac signal.

12. A rate responsive pacing system having a pacemaker device and a lead system interconnecting said device and a patient's heart, said device having a pulse generator for generating pacing pulses, sensing means for sensing cardiac signals connected from said heart by said lead system, sensor means for determining from received cardiac signals a sensor pacing rate, and rate control means for controlling said pulse generator to deliver pulses at said sensor rate, said sensor means comprising:

rate means for determining values of the patient's heart rate each cardiac cycle;

intrinsic means for obtaining QT intervals of intrinsic ventricular signals;

stim means for obtaining evoked QT intervals of stimulated ventricular signals;

compensating means for compensating said evoked QT intervals to obtain compensated QT intervals that correspond to intrinsic QT intervals;

reference means for constructing and storing a QT reference curve from said intrinsic QT intervals and said rate values; and calculating means for determining said sensor pacing rate from each respective QT and compensated QT interval.

13. The system as described in claim 12, wherein said compensating means comprises a stored constant value and an adjustment algorithm for adjusting the evoked QT by said stored value.

14. The system as described in claim 12, comprising differential means for storing data representing the difference between intrinsic QT and evoked QT as a function of rate.

15. The system as described in claim 12, wherein said intrinsic means comprises algorithm means for calculating a measure of the T wave portion of a received intrinsic signal;

comparing means for comparing said measure with a predetermined criterion to detect the occurrence of an intrinsic T wave; and timing means for determining the QT time of an intrinsic signal having a detected T wave.

16. The system as described in claim 15, wherein said algorithm means comprising integrating means for integrating said signal within a predetermined time following the R portion of said signal.

17. The system as described in claim 16, wherein said comparing means comprises threshold means for comparing said integration with a predetermined threshold value.

18. The system as described in claim 16, wherein said timing means comprises means for obtaining the slope of said T wave portion and for determining the peak value of said slope.

19. A method of controlling the pacing rate of a pacing system implanted in a patient, comprising:

sensing intrinsic patient ventricular signals;

determining from each said sensed signal the time of the R wave and calculating and storing the rate of each last cardiac cycle;

analyzing each said sensed signal within a predetermined time window following the R wave time to determine at least one measure of said signal;

comparing said measure to at least one criterion and detecting the occurrence of a T wave as a function said comparing;

for said detected T wave, determining the time between said R wave and said T wave and storing said time as a value of intrinsic QT;

storing a QT reference curve that provides reference values QT as a function of rate;

comparing each determined value of QT to said reference curve and determining therefrom an indicated pacing rate;

controlling the rate of pacing as a function of said indicated pacing rate;

storing values of intrinsic QT and rate corresponding to each detected T wave, and periodically recalculating said QT reference curve as a function of said stored values; and determining when a sensed ventricular signal represents an ectopic beat, and inhibiting determination and storing of a QT value for any such ectopic beat.

20. The method as described in claim 19, comprising determining the occurrence of a predetermined property of a said detected T wave, and storing the time between said R wave and said occurrence as the value of QT.

21. The method as described in claim 20, comprising obtaining the slope of said sensed signal following the R wave, and determining the time of the maximum of said slope.

22. The method as described in claim 21, comprising initiating a time window a predetermined number of ms following the time of said R wave.

23. The method as described in claim 22, comprising integrating said sensed signal at the start of said time window.

24. The method as described in claim 23, comprising storing a threshold integration value, and continuing said integrating until the intergral reaches said threshold or said time window times out.

25. The method as described in claim 24, comprising detecting a T wave when said integral reaches said threshold.

26. A method of controlling the pacing rate of a pacing system implanted in a patient, comprising:

sensing intrinsic patient ventricular signals;

determining from each said sensed signal the time of the R wave and calculating and storing the rate of each last cardiac cycle;

analyzing each said sensed signal within a predetermined time window following the R wave time to determine at least one measure of said signal;

comparing said measure to at least one criterion and detecting the occurrence of a T wave as a function of said comparing;

for a said detected T wave, determining the time between said R wave and said T wave and storing said time as a value of intrinsic QT;

storing a QT reference curve that provides reference values of QT as a function of rate;

comparing each determined value of QT to said reference curve and determining therefrom an indicated pacing rate;

controlling the rate of pacing as a function of said indicated pacing rate; and determining when there has been a delivered ventricular pace, determining a value of evoked QT for the evoked QRST following a delivered ventricular pace, and compensating said evoked QT to correct for the longer time of an evoked QT compared to an intrinsic QT.

27. The method as described in claim 26, comprising storing values of rate and compensated QT following a delivered pace.

28. The method as described in claim 26, comprising periodically recalculating said QT reference curve as a function of stored values of intrinsic and compensated QT.

29. The method as described in claim 28, comprising storing values of QT and corresponding values of rate for ventricular events across the patient's rate spectrum, and downloading said QT and rate data to an external site for analysis.

30. A method of controlling the pacing rate of a pacing system implanted in a patient, comprising:

sensing intrinsic patient ventricular signals;

determining from each said sensed signal the time of the R wave and calculating and storing the rate of each last cardiac cycle;

analyzing each said sensed signal within a predetermined time window following the R wave time to determine at least one measure of said signal;

comparing said measure to at least one criterion and detecting the occurrence of a T wave as a function of said comparing:

for a said detected T wave, determining the time between said R wave and said T wave and storing said time as a value of intrinsic QT;

storing a QT reference curve that provides reference values of QT as a function of rate;

comparing each determined value of QT to said reference curve and determining therefrom an indicated pacing rate;

controlling the rate of pacing as a function of said indicated pacing rate; and determining values of evoked QT for evoked ventricular events, compensating said values of evoked QT to substantially equate them to intrinsic values, and determining indicated pacing rate by comparing any determined value of QT to said QT reference curve.

31. The method as described in claim 30, comprising storing values of intrinsic and evoked QT and corresponding rate values, and periodically recalculating said QT reference curve as a function of said stored values.

32. An implantable pacing system for pacing a patient, said system having a pacing generator that generates pacing pulses at a controllable pacing rate and a rate control subsystem for controlling pacing rate, said subsystem comprising:

signal circuitry for receiving and processing intrinsic patient ventricular signals;

R wave means for detecting the occurrence of an R wave;

T wave means for determining the occurrence of a T wave, said T wave means comprising measure means for obtaining a measure of each said intrinsic signal over a period of time following a detected R wave;

QT means for determining the intrinsic QT interval of an intrinsic signal having a detected R wave and a detected T wave;

rate control mans for controlling pacing rate as a function of determined QT intervals;

DSP circuitry for providing the slope of said intrinsic signal following a detected T wave, and peak means for identifying the maximum value of said slope as the time of a T wave;

storage means for storing values of intrinsic QT and rate for each detected T wave;

reference means for calculating a QT reference curve as a function of said stored values; and DSP means for determining when a sensed ventricular signal represents an ectopic beat, and inhibiting means for inhibiting determining of a QT value for any such ectopic beat, wherein said T wave means further comprises storage that stores predetermined T wave criteria, and comparing means for comparing said measure with said criteria, and wherein said measure means comprises window means for initiating a window at a predetermined time following a detected R wave, and integrating means for integrating each said received intrinsic signal starting at the initiation of a said window.

33. An implantable pacing system for pacing a patient, said system having a pacing generator that generates pacing pulses at a controllable pacing rate and a rate control subsystem for controlling pacing rate, said subsystem comprising:

signal circuitry for receiving and processing intrinsic patient ventricular signals;

R wave means for detecting the occurrence of an R wave;

T wave means for determining the occurrence of a T wave, said T wave means comprising measure means for obtaining a measure of each said intrinsic signal over a period of time following a detected R wave;

QT means for determining the intrinsic QT interval of an intrinsic signal having a detected R wave and a detected T wave;

rate control mans for controlling pacing rate as a function of determined QT intervals;

means for determining the QT interval of evoked ventricular beats and for storing data representative of said evoked QT intervals; and means for compensating values of QT interval of evoked beats to substantially equate such values with intrinsic values of QT interval.

34. The system as described in claim 33, comprising storage means for storing determined intrinsic and evoked QT intervals, and reference means for constructing a QT reference curve from said stored values.

* * * * *